(12) United States Patent
Deuel

(10) Patent No.: US 11,759,223 B2
(45) Date of Patent: Sep. 19, 2023

(54) ARTICULATION LOCKING MECHANISMS FOR END EFFECTORS AND METHODS OF USE

(71) Applicant: Boston Scientific Scimed, Inc, Maple Grove, MN (US)

(72) Inventor: Christopher R. Deuel, Melrose, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 151 days.

(21) Appl. No.: 17/165,669

(22) Filed: Feb. 2, 2021

(65) Prior Publication Data
US 2021/0236152 A1 Aug. 5, 2021

Related U.S. Application Data

(60) Provisional application No. 62/969,738, filed on Feb. 4, 2020.

(51) Int. Cl.
*A61B 17/29* (2006.01)
*A61B 17/072* (2006.01)

(52) U.S. Cl.
CPC .... *A61B 17/29* (2013.01); *A61B 2017/07257* (2013.01); *A61B 2017/07271* (2013.01); *A61B 2017/07278* (2013.01); *A61B 2017/07285* (2013.01); *A61B 2017/2946* (2013.01)

(58) Field of Classification Search
CPC ........................ A61B 17/29; A61B 2017/2946
See application file for complete search history.

(56) References Cited

U.S. PATENT DOCUMENTS

2015/0374365 A1 12/2015 Schuckmann et al.
2017/0224330 A1* 8/2017 Worthington .... A61B 17/07207

FOREIGN PATENT DOCUMENTS

EP 3 064 143 A1 9/2016
EP 3 205 272 A1 8/2017

* cited by examiner

*Primary Examiner* — Shaun L David
*Assistant Examiner* — Rachael L Geiger
(74) *Attorney, Agent, or Firm* — Bookoff McAndrews, PLLC

(57) ABSTRACT

A medical device includes an end effector at a distal end of the medical device, an actuator coupled to a proximal end of the end effector, a pivot arm pivotally coupled to the end effector distal of the proximal end of the end effector, where actuation of the actuator pivots the end effector relative to the pivot arm, and a lock on the end effector and the pivot arm, where the lock has a first state permitting the end effector to pivot relative to the pivot arm and a second state restricting the end effector from pivoting relative to the pivot arm.

14 Claims, 7 Drawing Sheets

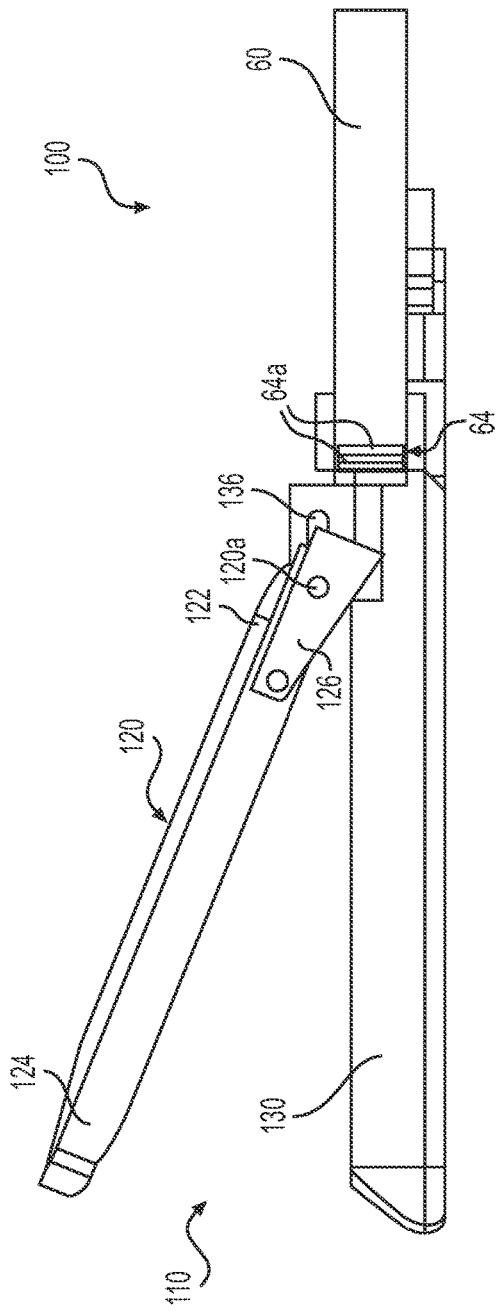
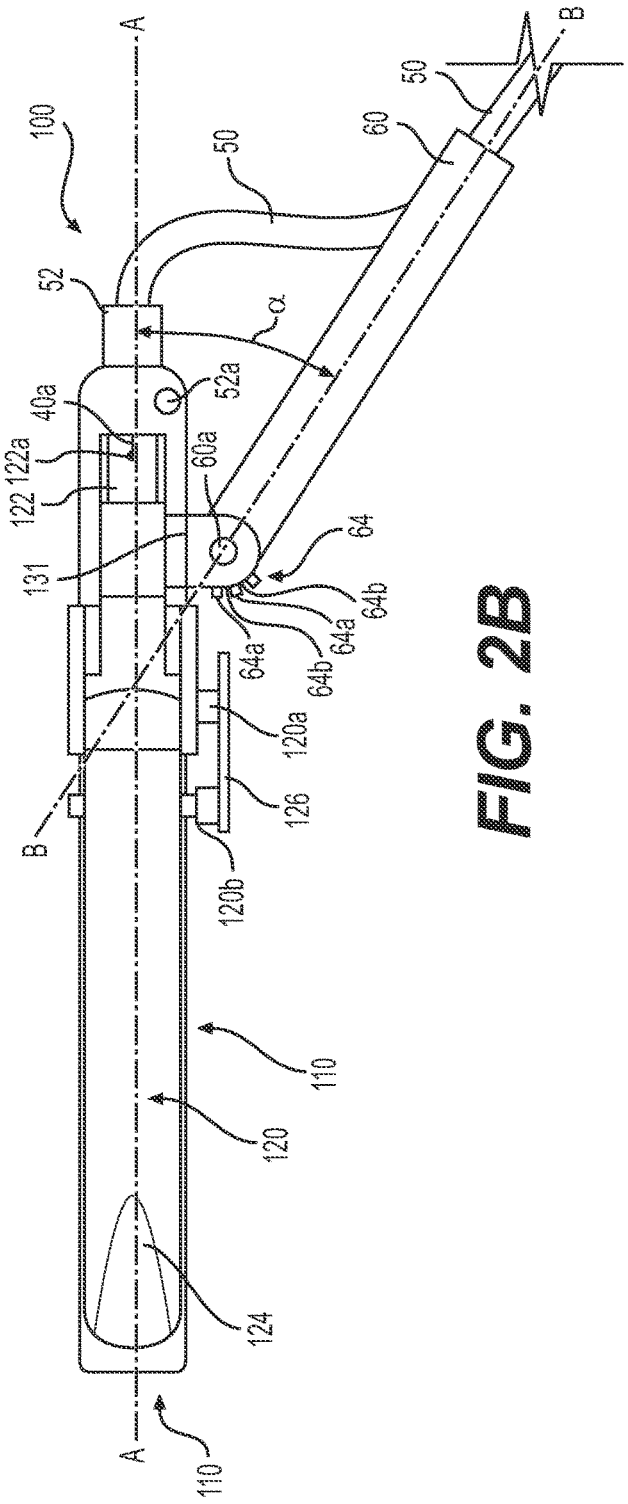
FIG. 2A
FIG. 2B

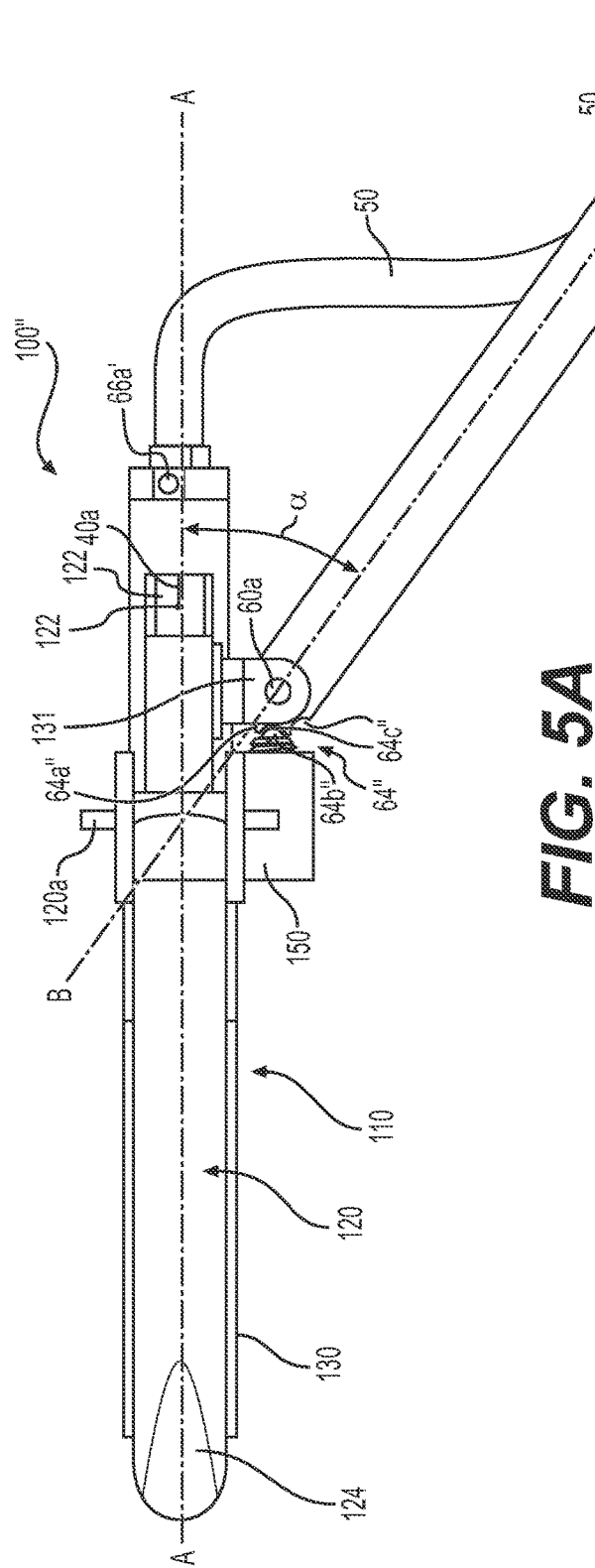
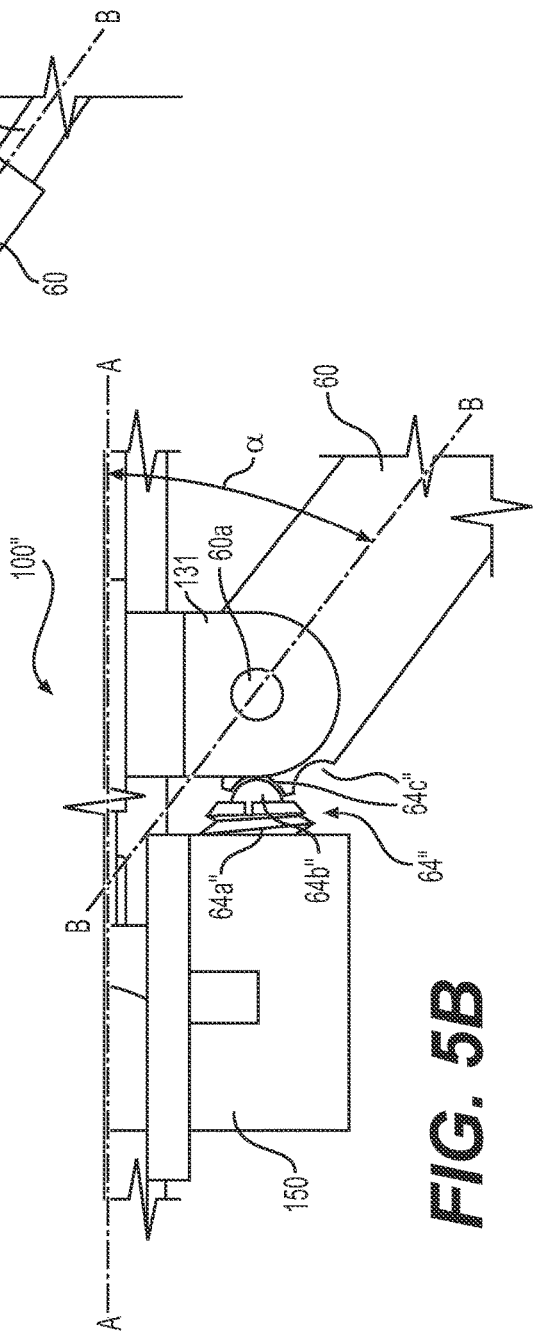

ARTICULATION LOCKING MECHANISMS FOR END EFFECTORS AND METHODS OF USE

CROSS-REFERENCE TO RELATED APPLICATIONS

This application claims the benefit of priority from U.S. Provisional Application No. 62/969,738, filed on Feb. 4, 2020, which is incorporated by reference herein in its entirety.

TECHNICAL FIELD

This disclosure relates to minimally invasive (e.g., endoscopic and/or laparoscopic) medical devices and related methods of use. In embodiments, the disclosure relates to one or more locking mechanisms for end effectors, e.g., tissue fastening devices such as stapler devices, and related methods of use, among other aspects.

BACKGROUND

Technological developments have given users of medical systems, devices, and methods, the ability to conduct increasingly complex procedures on patients. The grasping and/or coupling of tissue in a patient's body, for example, may be performed by surgical devices that grasp or clamp tissue between opposing jaw structures and then fasten or cut the tissue. A drawback of these systems may include, for example, maintaining a desired orientation of the jaws of an end effector during a procedure, such as a stapling procedure, a cutting procedure, and/or additional medical procedures. For example, to access tissue, an end effector may be articulated about a pivot point. During a cutting or a fastening step, actuation of the cutting and/or fastening device may cause the end effector to pivot from the selected orientation to a different, undesired orientation. Thus, tissue may not be properly stapled and/or cut, which may increase therapy time and/or cost, may cause undesired or incomplete fastening of tissues, and/or may require additional therapy/intervention at the target site. This disclosure may solve one or more of these problems or other problems in the art. The scope of the disclosure, however, is defined by the attached claims and not the ability to solve a specific problem.

SUMMARY OF THE DISCLOSURE

According to an aspect, a medical device includes an end effector at a distal end of the medical device, an actuator coupled to a proximal end of the end effector, a pivot arm pivotally coupled to the end effector distal of the proximal end of the end effector, where actuation of the actuator pivots the end effector relative to the pivot arm, and a lock on the end effector and the pivot arm, where the lock has a first state permitting the end effector to pivot relative to the pivot arm and a second state restricting the end effector from pivoting relative to the pivot arm.

The end effector may include a first jaw, and a second jaw hingedly connected to the first jaw and configured to move between an open position and a closed position.

The locking mechanism may include a plurality of teeth at a distal end of the pivot arm, wherein the plurality of teeth may define a plurality of spaces, and a tab connected to the end effector, wherein the tab may be configured to engage a space from the plurality of spaces in the second state.

The lock is in the first state when the pair of jaws is in the open position, and the lock is in the second state when the pair of jaws is in the closed position.

The end effector may be configured to pivot independently of a movement of the first jaw relative to the second jaw.

The locking mechanism may include a sprocket connected to the pivot arm, wherein the sprocket may include a plurality of teeth defining a plurality of spaces, and a pawl pivotally connected at the proximal end of the end effector and may be configured to engage the plurality of spaces.

The medical device may further comprise a wire connected to the pawl and extending in a proximal direction, wherein the pawl may be biased into engagement with the plurality of spaces of the sprocket, and wherein moving the wire in the proximal direction may be configured to pivot the pawl away from the sprocket to disengage the pawl from the plurality of spaces.

The sprocket may be arc shaped, and wherein a convex arrangement of the plurality of spaces of the sprocket may face proximally.

The locking mechanism may include a ball-nose spring plunger.

The ball-nose spring plunger may include a spring coupled at a first end of the end effector, wherein the spring may be configured to extend from the first end and compress along a compression axis, a plurality of detents fixed to the pivot arm, and a ball bearing connected to the spring and selectively engaging each of the plurality of detents, wherein the ball bearing may be configured to move along the compression axis.

The ball bearing may be configured to move from a first detent of the plurality of detents to an adjacent, second detent of the plurality of detents as the end effector pivots about the pivot arm, and wherein the spring may be configured to be compressed from a first position to a second position and expand back to the first position as the ball bearing moves from the first detent to the second detent.

The medical device may further comprise an actuation wire fixed to a proximal end of the end effector, wherein actuation of the actuation wire may be configured to move the end effector between an open position and a closed position.

The pivot arm may include a first opening at a proximal end of the pivot arm, a second opening in a sidewall of the pivot arm, and a lumen extending from the first opening to the second opening. The actuator may be configured to extend through each of the first opening, the lumen, and the second opening.

The medical device may further comprise a handle assembly configured to actuate the end effector and the locking mechanism, wherein a proximal end of the actuator may be connected to a distal end of the handle assembly, and a catheter may include at least one lumen and may extend distally from the handle assembly, wherein the actuator may extend through the at least one lumen, and wherein the pivot arm may be fixed to a distal end of the catheter.

A pivot angle may be defined between a longitudinal axis of the end effector and a longitudinal axis of the pivot arm, wherein a distal movement of the actuator may be configured to increase the pivot angle, and wherein a proximal movement of the actuator may be configured to decrease the pivot angle.

According to another aspect, a medical device comprises an elongated member, an end effector connected to a distal end of the elongated member, wherein the end effector may include a tab, and a catheter including a plurality of spaces at a distal end, wherein the tab may be configured to selectively engage the plurality of spaces to inhibit pivotal movement of the end effector.

The elongated member may extend through an opening of the catheter proximally of a distal end of the catheter, and wherein the end effector may be pivotally coupled to the catheter distally of the opening.

According to another aspect, a medical method includes advancing an end effector and a pivot arm to a target site within a patient, pivoting the end effector relative to the pivot arm about a pivot axis until a desired orientation of the end effector is achieved, locking the orientation of the end effector relative to the pivot arm, and performing an operation via the end effector.

The end effector may include a first jaw, and a second jaw hingedly connected to the first jaw, wherein the end effector may include an open configuration and a closed configuration, and wherein a distance between distal ends of the first jaw and the second jaw may be greater in the open configuration than a distance between the distal ends of the first jaw and the second jaw in the closed configuration.

When the end effector is in the closed configuration, the end effector may be locked relative to the pivot arm, and when the end effector is in the open configuration, the end effector may be unlocked relative to the pivot arm.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 2A and 2B are views of an end effector of the fastening device of FIG. 1, according to an embodiment;

FIG. 5A is a view of an end effector of the fastening device of FIG. 1, according to another embodiment; and FIG. 5B is a view of a locking mechanism of the end effector of FIG. 5A.

DETAILED DESCRIPTION

Figure 1:
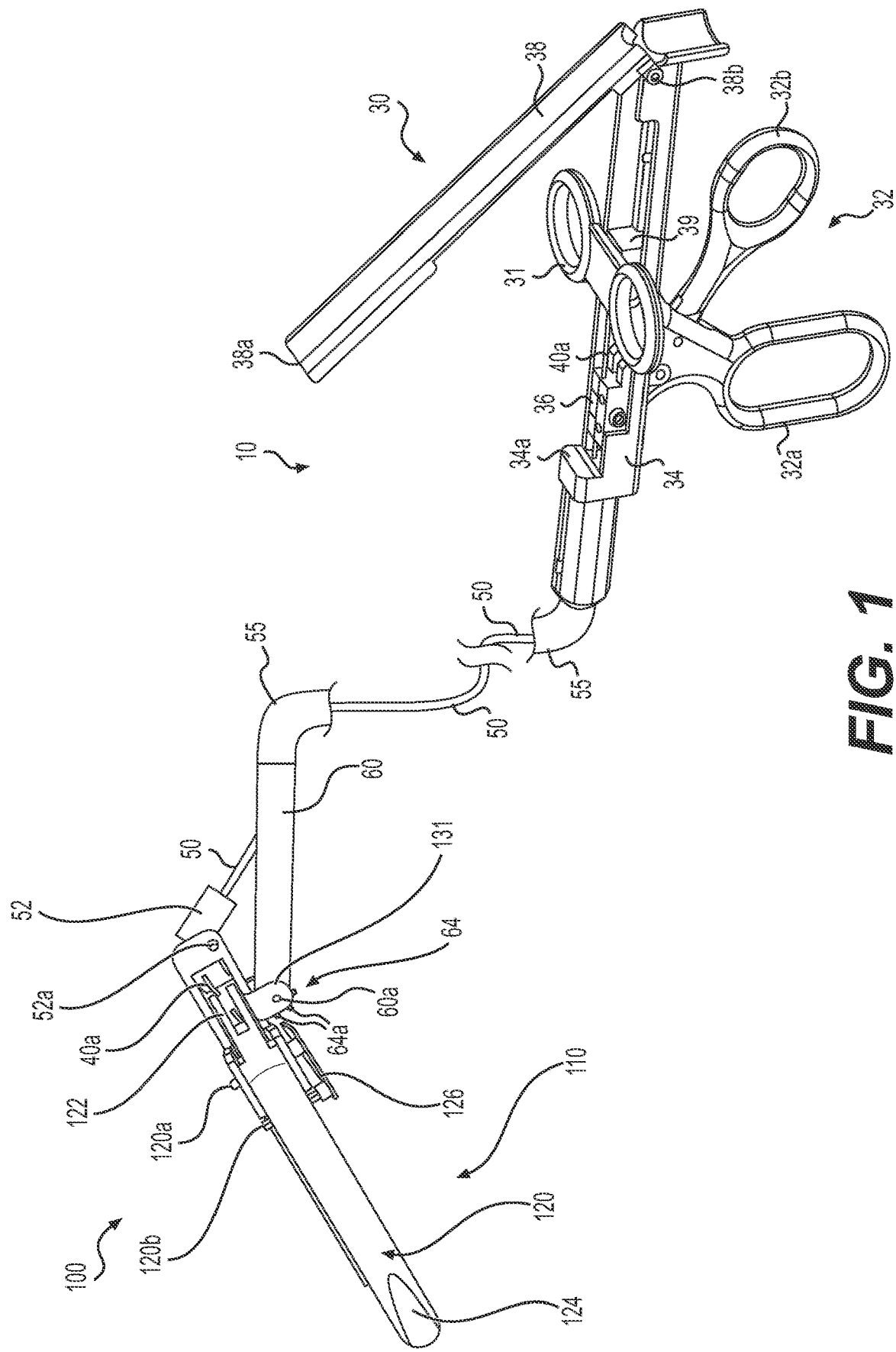
FIG. 1 is a schematic view of a tissue fastening device according to an embodiment.

This disclosure is described with reference to exemplary medical systems and medical tools for accessing a target site, for example, for grasping, cutting, and/or stapling tissue. This may provide improved medical tool functionality and/or may assist medical professionals to improve cutting and/or fastening of tissue. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. This disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Additionally, terms that indicate the geometric shape of a component/surface refer to exact and approximate shapes.

Embodiments of this disclosure may be used to cut and/or fasten tissue in an endo-luminal space, or facilitate the process thereof. According to an example, the fastening device may be a tissue stapling apparatus, which may include a resection or cutting mechanism (e.g., an integrated knife) and a stapling mechanism (e.g., a stapler). The fastening device may be delivered through an endoscope working channel to the target tissue site. All or parts of the fastening device could be metallic (such as stainless steel, titanium, or cobalt chrome), plastic (such as polyetheretherketone (PEEK) or the like), or include a shape memory metal (such as nitinol), a shape memory polymer, a polymer, or any combination of materials. While reference is made herein to a fastening device, the described locking members may be used with any device pivotally connected to a distal end of a catheter, sheath, tube, or the like. The locking members may prevent pivotal movement of an end effector or other device pivotally connected to the distal end of, e.g., the catheter. This may improve an operation of the end effector. For example, preventing a pivotal rotation of a stapler during stapling may improve the connection between the adjacent tissues.

FIG. 1 shows an apparatus 10 in accordance with an example of this disclosure. Apparatus 10 may be a surgical stapling apparatus configured to engage body tissue, and apply a plurality of fasteners thereto during minimally invasive procedures, such as laparoscopic or endoscopic procedures. In some embodiments apparatus 10 may be a suturing apparatus to delivering a suture for tissue closure during minimally invasive surgical procedures. Apparatus 10 may be used to apply a suture, clips, or other fasteners, but will be primarily discussed in the context of grasping tissue in preparation of performing additional procedures to the tissue, e.g., stapling and/or cutting the tissue.

As illustrated in FIG. 1, apparatus 10 includes a handle assembly 30 at a proximal end, an end effector 100 at a distal end, and an elongated body 50 (e.g., a catheter or the like) connecting a distal end of handle assembly 30 to a proximal end of end effector 100 (as will be explained herein, end effector 100 may include a stapler device 110). Elongated body 50 may extend any length suitable for endoscopic or laparoscopic procedures, and may be configured to be positioned within a working channel of an endoscope. Alternatively, elongated body 50 may extend along an outer surface of the endoscope if, for example, the endoscope includes only a single lumen and/or a diameter of the lumen(s) of the endoscope are too small to receive elongated body 50. Elongated body 50 may be detachable from handle assembly 30 to facilitate insertion of elongated body 50 into a working channel of an endoscope or a channel of another device, for example by backloading elongated body 50 into the working channel. In some examples, elongated body 50 may be flexible, steerable, and/or may be rotatable about its axis. Elongated body 50 may include a lumen (or multiple lumens) for positioning actuation wires within, for actuating end effector 100 via handle assembly 30 or actuating any other portion of apparatus 10. Elongated body 50 may be configured to receive a plurality of actuation wires or a single actuation wire. In some examples, elongated body 50 may be fixedly coupled to end effector 100, and in other examples elongated body 50 may be removably or releasably coupled to end effector 100. Unless stated otherwise, any wire or actuation device described herein may extend from handle assembly 30 to end effector 100 via a lumen of elongated body 50. Alternatively, or additionally, one or more of these actuation wires or devices may extend from handle assembly 30 to end effector 100 outside of (e.g., adjacent to) elongated body 50. A catheter 55 (or any other sheath) including a lumen may extend distally from a distal end of handle assembly 30. Elongated body 50 may be disposed within the lumen of catheter 55 and may move relative to catheter 55. While catheter 55 is shown with a curved region in FIG. 1, catheter 55 may be a straight sheath (e.g., such as a hypotube) having a rigidity sufficient to be moved proximally and distally within the body. Additionally, FIGS. 2A-2C, 3A, 3B, 4A, 4B, 5A, and 5B may be shown without catheter 55 attached to the proximal end of a pivot arm 60 for ease of understanding (e.g., to visualize elongated body 50).

Handle assembly 30 may include a handle 32 and a body 34. Handle 32 may include a fixed portion 32a and an actuator portion 32b. Fixed portion 32a of handle 32 may be fixedly coupled to body 34. Actuator portion 32b may include a circular or oval portion or ring for positioning a user's finger within, which may assist a user in holding handle assembly 30. In some examples, actuator portion 32b of handle 32 may be an actuator which may be pivotally coupled to body 34 and movable relative to fixed portion 32a of handle 32. In some examples, actuator portion 32b of handle 32 may be coupled to a proximal portion of an actuation wire, such as an actuation wire 40a, via an adjustable coupler 36, as will be described herein. An anvil 120 of stapler device 110 may be actuated via actuation wire 40a, which extends between stapler device 110 and handle assembly 30. In other examples, actuator portion 32b of handle 32 may be configured to control any other mechanism of apparatus 10, such as operating an articulation lock of end effector 100, actuation of the deployment of staples from stapler device 110, or the like. It will be understood that wire 40a may have sufficient rigidity to be pushed in the distal direction and pulled in the proximal direction.

In some examples, handle assembly 30 may include a moveable cover 38 pivotally coupled to housing 34 at pivot point 38b. In FIG. 1, cover 38 is shown in an open position, exposing the internal portions of body 34. Cover 38 may be coupled to a proximal portion of body 34 and may cover the internal components of handle assembly 30 when positioned in a closed configuration, e.g., when a distalmost end 38a of cover 38 faces a surface 34a of body 34. Cover 38 may be positioned to cover the internal components of body 34 (e.g., a closed configuration) via a coupling mechanism at a distal portion of cover 38 and a distal portion of handle assembly 30, such as a snap-fit mechanism or the like. When in the closed configuration, cover 38 may form a pair of slots in body 34 (not shown). When the distal portion of cover 38 is uncoupled from the distal portion of body 34, a user may rotate or pivot cover 38 at pivot point 38b in order to access to the internal components of handle assembly 30.

Handle assembly 30 may include one or more adjustable couplers 36, 39, which may be configured to receive a portion of an actuation wire, such as actuation wire 40a. Any of adjustable couplers 36, 39 may be a vice which is moveable in order to clamp down onto actuation wire 40a and fixedly couple actuation wire 40a to the adjustable couplers 36, 39. In some examples, adjustable couplers 36, 39 may be moveable via a screw to adjust couplers 36, 39 and couple or uncouple actuation wire 40a from couplers 36, 39. Couplers 36, 39 may be used in the movement of additional wires described herein.

Adjustable coupler 39 may be coupled to longitudinal actuator 31 and moveable longitudinally via translating longitudinal actuator 31 within body 34. Longitudinal actuator 31 may be partially positioned within housing 34 and may be slidable longitudinally within the two slots formed when cover 38 is positioned over the internal components of handle assembly 30. Longitudinal actuator 31 may include a pair of opposing circular or oval portions or rings, with each circular portion defining an aperture for a user to position a respective finger within. In some examples, longitudinal actuator 31 may be coupled to an actuation wire (not shown), such as via adjustable coupler 39 or via a different coupler within body 34, and may be configured to control staple deployment from stapler device 110. In other examples, longitudinal actuator 31 may be configured to control any other mechanism of apparatus 10, such as actuation of an anvil 120 of stapler device 110, actuation of a locking mechanism associated with end effector 100, or the like.

With continued reference to FIG. 1, end effector 100 includes stapler device 110 which may be pivotally coupled to the distal end of elongated body 50. For example, a connector 52 at a distal end of elongated body 50 may be pivotally attached to a proximal end of stapler device 110 via a pin 52a or the like. A pivot arm 60 may be pivotally attached to a side of a body 130 of stapler device 110 via a pin 60a. For example, one or more protrusions 131 may extend from the side of body 130 and may receive pin 60a through an opening in protrusion 131, thereby fixing pin 60a relative to protrusion 131. Pin 60a defines a pivot axis of stapler device 110 relative to pivot arm 60. Pin 60a may also be received in an opening 66 at a distal end of pivot arm 60 (FIG. 2C), which may allow stapler device 110 to pivot relative to pivot arm 60. Pivot arm 60 may be fixedly attached to a distal end of catheter 55 by ultrasonic welding, adhesive, crimping, or the like. This may prevent pivot arm 60 from moving when elongated member 50 is moved relative to catheter 55 and/or pivot arm 60, as will be described herein. For ease of understanding, catheter 55 is shown only in FIG. 1.

Figure 2C:
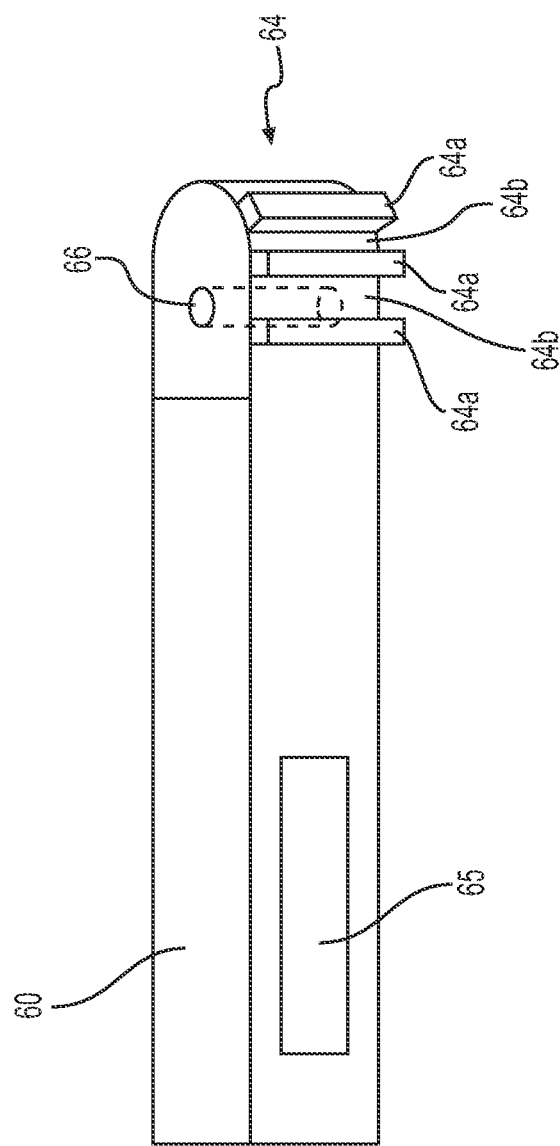
FIG. 2C is a view of a pivot arm of the end effector of FIGS. 2A and 2B.

As shown in FIG. 2A, pivot arm 60 may include an opening 62 at a proximal end. Opening 62 may be connected to a lumen extending from the proximal end to the distal end of arm 60. A slot 65 (e.g., an opening) (FIG. 2C) may be formed in a side of pivot arm 60 and may be connected to the lumen of pivot arm 60. Slot 65 may be oval, rectangular, or any other suitable shape. Opening 62, the lumen of pivot arm 60, and slot 65 may be sized and shaped to receive a portion of elongated body 50, such that elongated body 50 may enter pivot arm 60 via opening 62 and extend out of slot 65. As will be described herein, movement of elongated body 50 relative to pivot arm 60 may cause stapler device 110 to rotate relative to pivot arm 60. Pivot arm 60 shown in FIG. 2C, or aspects of pivot arm 60 including slot 65, may be used with any end effector described herein. While pivot arm 60 is shown as a rectangular prism, pivot arm 60 may be any shape, including a cylinder, a rectangular prism with rounded edges, or the like.

Anvil 120 may be rotatably or pivotally coupled to body 130 via pin 120a (pin 120a may define a pivot axis). Anvil 120 and body 130 may be collectively referred to as jaws, grasping elements, and/or opposing members. Anvil 120 may extend distally towards a distal end of stapler device 110 from pin 120a. In some examples, anvil 120 may be rotatably biased about pin 120a and may be biased in an open configuration. For example, a distal end 124 of anvil 120 may biased away from body 130 using a spring or the like, thereby creating a space between distal end 124 of anvil 120 and a distal portion of body 130. Anvil 120 may rotate about pin 120a and may contact or may approach body 130 in a closed position, e.g., to retain tissue between anvil 120 and body 130. In some examples, body 130 may include a channel that supports a cartridge of staples or other fastening devices (not shown). The closed position of anvil 120 may provide a surface for which staples may be driven against when ejected from the cartridge of stapler device 100. The cartridge may contain a plurality of surgical fasteners, such as staples, and the fasteners may be deployed from the cartridge when under the influence of a driving force exerted by an actuation sled or other actuation mechanism. Suitable staplers and associated actuation mechanisms are described in commonly-owned U.S. Provisional Patent Application No. 62/812,538, filed Mar. 1, 2019, the complete disclosure of which is incorporated herein by reference.

With reference to FIGS. 2A and 2B, pin 120a may extend from a side of anvil 120, and pin 120a may be disposed in a slot 136 on a side of body 130. For example, slot 136 may be disposed in an upper extension of body 130. In addition to pivoting about pin 120a, anvil 120 may move in a longitudinal direction via pin 120a and slot 136. For example, pin 120a of anvil 120 may move within slot 136, which has a generally oval shape and extends in a longitudinal direction along a longitudinal axis. Slot 136 may be any shape, and may alternatively be a hole that fixes a longitudinal position of pin 120a. In the embodiment shown in FIGS. 2A and 2B, when pin 120a is located at a distal end of slot 136, anvil 120 may be positioned in the open configuration, and anvil 120 may be in the closed position when pin 120a is positioned at a proximal end of slot 136. Wire 40a may be attached at a proximal end 122 of anvil 120 via an attachment mechanism 122a. Proximal movement of wire 40a may cause anvil 120 to move proximally, which may cause anvil 120 to rotate about pin 120a into the closed position. Distal movement of wire 40a may cause anvil 120 to move distally, which may cause anvil 120 to rotate about pin 120a into the open position.

FIG. 2B illustrates a top view of end effector 100 in the open configuration. A locking tab 126 is connected to anvil 120 via pin 120a and a second pin 120b, distal of pin 120a. Through those connections locking tab 126 moves with anvil 120. It will be understood that locking tab 126 may be connected to anvil 120 via any other mechanism known in the art. According to an example, pin 120b may engage a second slot, distal to slot 136, in the closed configuration, which may lock anvil 120 in the closed configuration.

Pivot arm 60 may include a pivot head 64 at the distal end thereof. Pivot head 64 may include a plurality of teeth 64a defining a plurality of spaces 64b therebetween. Locking tab 126 may engage spaces 64b, as will be described herein. Teeth 64a and spaces 64b may be spaced apart radially about a circumference of pivot head 64 (FIG. 2C) such that stapler device 110 may be locked at an angle relative to pivot arm 60. For example, an angle α is defined as an angle between the longitudinal axis A-A of stapler device 110 and the longitudinal axis B-B of pivot arm 64. When a is 0 degrees, pivot arm 60 may be approximately parallel to stapler device 110 (axes A-A and B-B are approximately parallel), and when a is 90 degrees, pivot arm 60 may be approximately perpendicular to stapler device 110 (axes A-A and B-B are approximately perpendicular). According to an example, teeth 64a and spaces 64b may be spaced such that stapler device 110 may be locked at an orientation relative to pivot arm 60 such that a may be one of approximately 0 degrees, approximately 30 degrees, approximately 60 degrees, and approximately 90 degrees. It will be understood that a is not limited to these angles. The number of teeth 64a and spaces 64b, and their spacing, may determine the various angles α of locking stapler device 110 relative to pivot head 64. For example, teeth 64a may be positioned on pivot head 64 to change the angle of a. Further, the number of teeth 64a is not limited to three teeth 64a, as shown in FIGS. 2A and 2B, and may be chosen based on the number of designed locking angles.

Figure 3A:
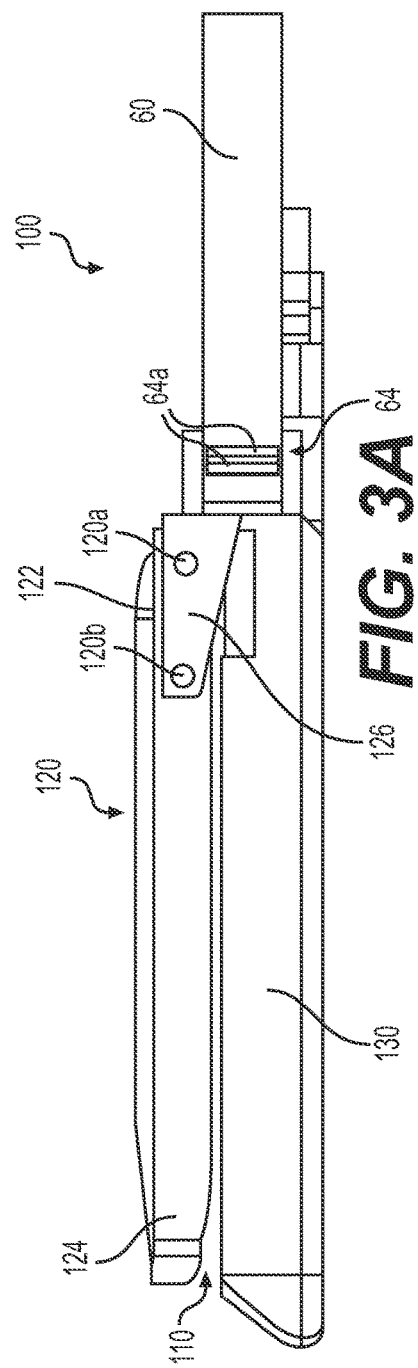
FIGS. 3A and 3B are views of an end effector of the fastening device of FIG. 1, according to an embodiment.
Figure 3B:
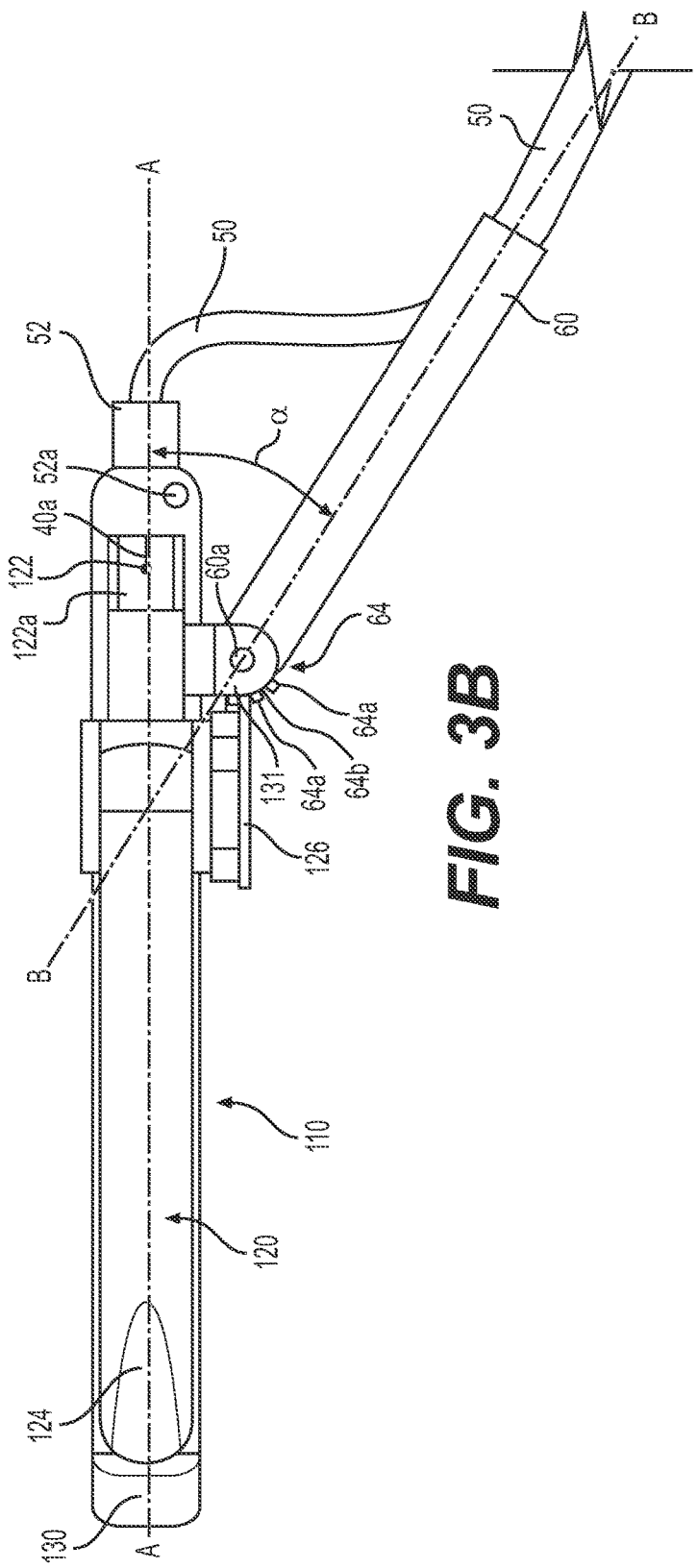

FIGS. 3A and 3B illustrate anvil 120 in the closed configuration. In the closed configuration, anvil 120 has rotated about pin 120a such that distal end 124 of anvil 120 is closer to body 130 than in the open configuration. As shown in FIG. 3B, locking tab 126 may communicate with teeth 64a in the closed position to prevent relative rotational or pivotal movement between stapler device 110 and pivot arm 60. For example, a proximal portion of locking tab 126 may be positioned between adjacent teeth 64a in the closed configuration, which may prevent stapler device 110 from rotating relative to pivot arm 60.

A method of operating end effector 100 will now be described. End effector 100 may be advanced to a target site in a body via an incision or a natural orifice. End effector 100 is advanced in a closed configuration and subsequently opened via actuation of actuation wire 40a. In the open configuration, tissue at the target site may be placed between anvil 120 and body 130 (e.g., jaws) of stapler device 110, via any suitable method. To properly orient stapler device 110, a user may push distally or pull proximally on elongated body 50 to cause stapler device 110 to pivot about the axis defined by pin 60a until a desired orientation of stapler device 110 relative to pivot arm 60 is achieved (e.g., a desired angle α). The desired positioning/orientation of stapler device 110 may be assisted by an imaging device associated, for example, with an endoscope through which apparatus 10 is inserted. After the desired orientation is achieved, the user may move wire 40a in a proximal direction (e.g., pull on wire 40a) and thereby move anvil 120 into the closed configuration using, e.g., handle assembly 30. As anvil 120 moves into the closed configuration, locking tab 126 may engage spaces 64b in a locked position and may prevent rotation of stapler device 110 about the axis defined by pin 60a. While in this locked position, the user may perform additional procedures, e.g., stapling, cutting, or other procedures on the tissue. Once the procedure is complete, the user may move (e.g., push) wire 40a in a distal direction, which may cause anvil 120 to move to the open position, thereby disengaging locking tab 126 from spaces 64b. The user may then rotate stapler device 110 to a new, different orientation relative to pivot arm 60. If desired, the user may relock stapler device 110 in the new orientation by repeating this procedure or the user may remove the apparatus from the body.

Figure 4A:
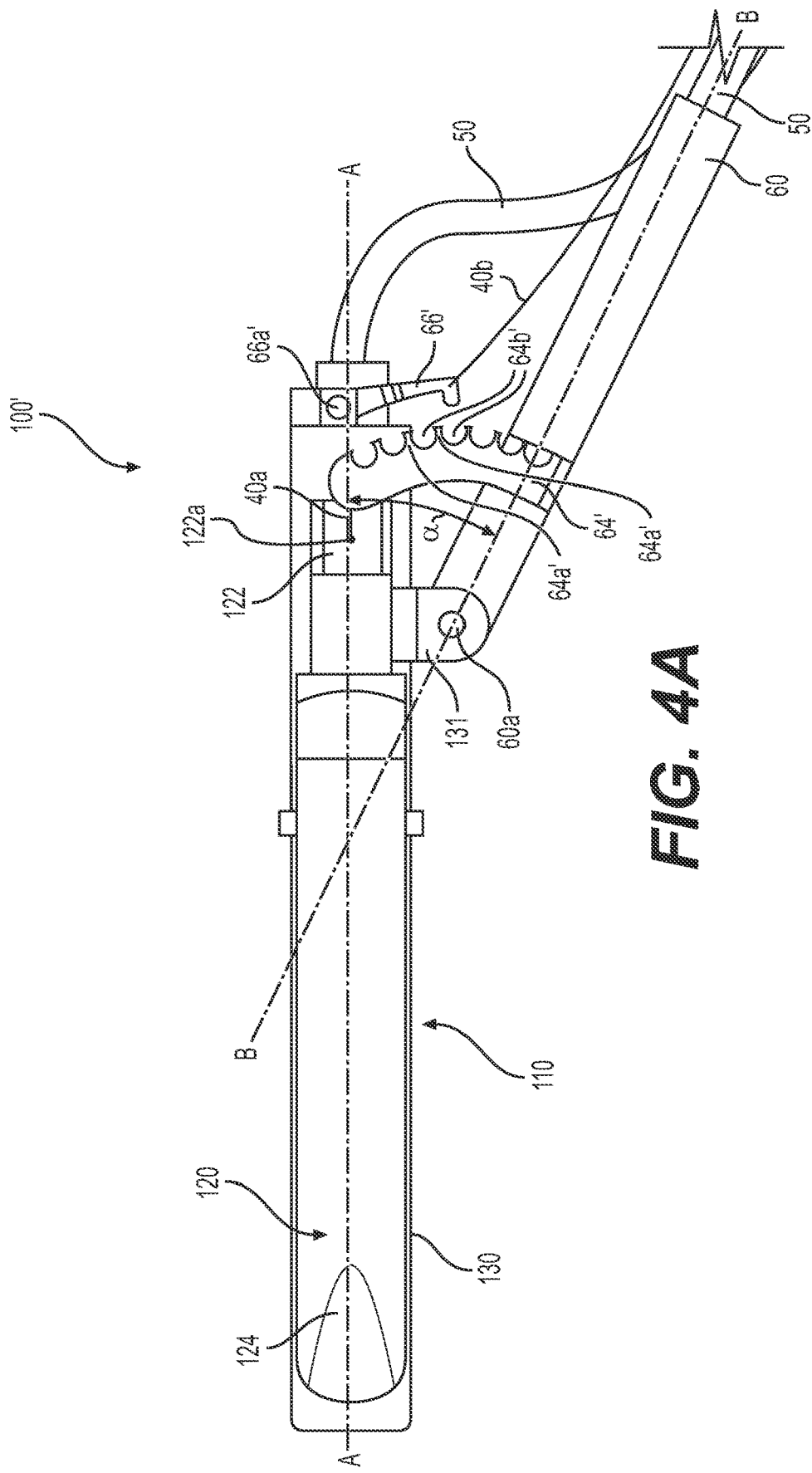
FIGS. 4A and 4B are views of an end effector of the fastening device of FIG. 1, according to another embodiment.
Figure 4B:
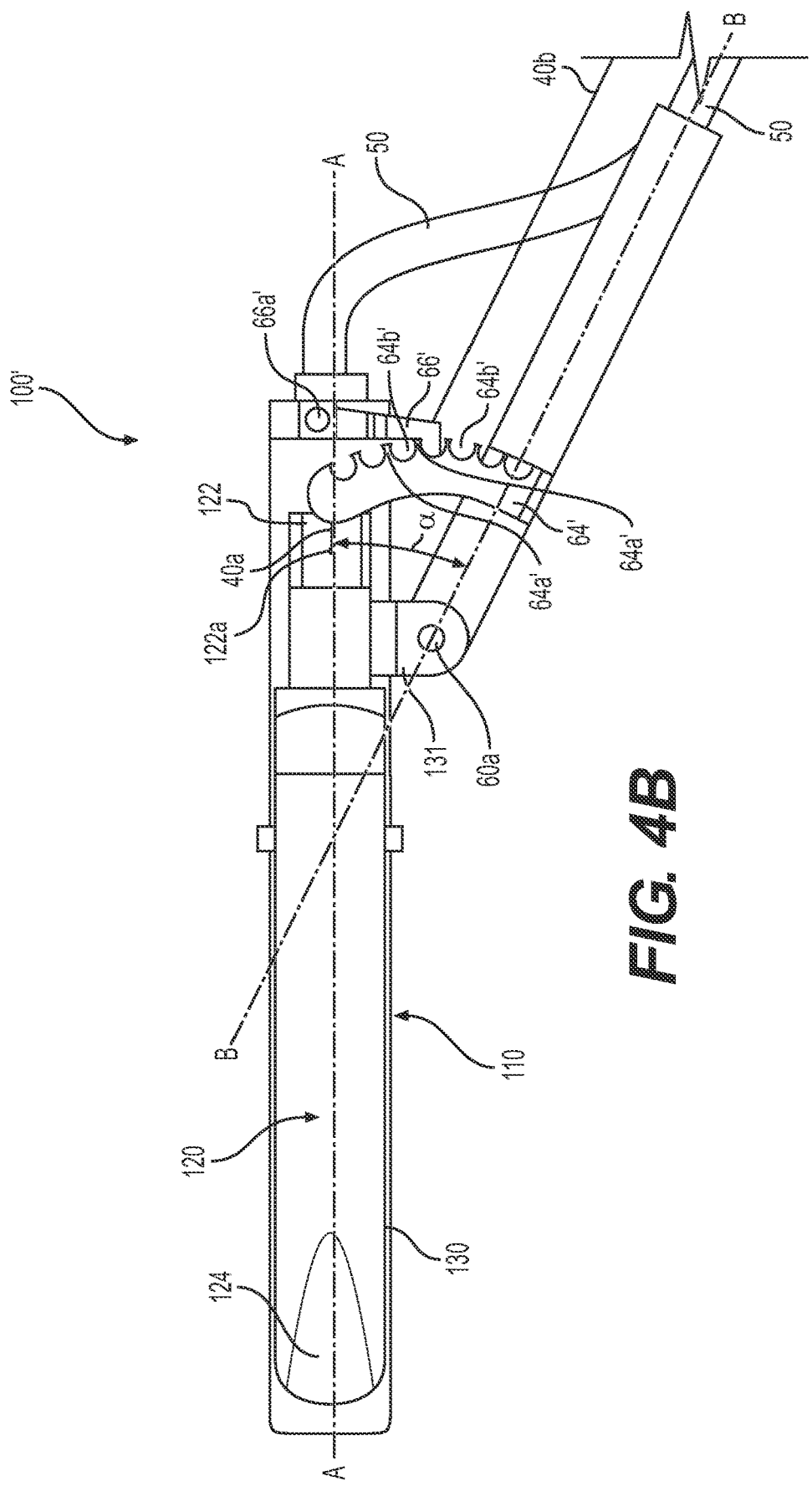

A locking mechanism for an end effector 100' according to another example is shown in FIGS. 4A and 4B. End effector 100' is similar to end effector 100, and may include stapler device 110 pivotally connected to pivot arm 60. Locking mechanism may include a pawl 66' and a sprocket 64' having a plurality of teeth 64a'. Spaces 64b' are defined between adjacent teeth 64a'. Sprocket 64' may be rigidly connected to pivot arm 60 and may have an arc shape with a convex surface facing a proximal end of the end effector 100. Pawl 66' may be pivotally attached to body 130 of end effector 100 by a pin 66a'. A biasing member, e.g., a spring, may bias pawl 66' in a distal direction, e.g., toward sprocket 64'. Pawl 66' may engage spaces 64b' to lock stapler device 110 in a desired orientation relative to pivot arm 60. For example pawl 66' may sit in any one of spaces 64b' between adjacent teeth 64a'. An actuation wire 40b may be attached to an end of pawl 66' opposite an end of pawl 66' connected to pin 66a'. Actuation wire 40b may be similar to wire 40a and may be moved proximally (e.g., pulled) and distally (e.g., pushed) to cause pawl 66' to pivot about pin 66a'.

As with end effector 100, end effector 100' may be locked such that an orientation of stapler device 110 relative to pivot arm 60 is locked at one or more positions based on the number of teeth 64a' and spaces 64b', and the spacing of teeth 64a' and spaces 64b'. For example, when a is 0 degrees, pivot arm 60 may be parallel to end effector 100' (axes A-A and B-B are approximately parallel), and when α is 90 degrees, pivot arm 60 may be perpendicular to end effector 100' (axes A-A and B-Bare approximately perpendicular). It will be understood that angle α is not limited to these angles. Further, teeth 64a' and spaces 64b' are not limited to the number shown in FIGS. 4A and 4B. The number of teeth 64a' and the number of spaces 64b' may be selected based on the number of possible positions stapler device 110 may be locked relative to pivot arm 60. For example, teeth 64a' define seven spaces 64b' that provide different angles α between axes A-A and B-B. More or fewer spaces 64b' at different spacing may provide different angular adjustments of stapler device 110.

A method of operating end effector 100' will now be described. End effector 100' may be introduced to the body and advanced to the target site in a similar manner as end effector 100. Pawl 66' is engaged with a space 64b' during insertion, so that angle α is approximately 0 degrees. Once end effector 100' is adjacent the target site, the user may move actuation wire 40b in a proximal direction by, e.g., pulling on actuation wire 40b. Proximal movement of actuation wire 40b may cause pawl 66' to rotate about pin 66a' and disengage pawl 66' from a space 64b' and teeth 64a' of sprocket 64'. After pawl 66' is disengaged from space 64b' and teeth 64a', the user may orient stapler device 110 as desired relative to the tissue and/or target site in a manner similar to orienting stapler device 110 as discussed with reference to FIGS. 2A and 2B, e.g., by moving elongated body 50 in a proximal or distal direction, thereby changing angle α. Once stapler device 110 is properly oriented, the user may release and/or push actuation wire 40b in the distal direction. For example, if pawl 66' is biased toward sprocket 64', releasing actuation wire 40b may cause pawl 66' to engage a space 64b' between teeth 64a'. Alternatively, or additionally, a distal force applied to actuation wire 40b may be necessary for such engagement. Once pawl 66' engages a space 64b' between teeth 64a', stapler device 110 may be locked in the selected orientation and the user may perform additional procedures. For example, the user may then move anvil 120 from the open configuration to the closed configuration by moving actuation wire 40a proximally and/or may perform additional medical procedures, e.g., stapling, cutting, or other procedures on the tissue. To change the orientation of stapler device 110 relative to pivot arm 60, pawl 66' may again be disengaged from teeth 64a' and stapler device 110 may be rotated about the axis defined by pin 60a as described herein. Locking mechanism 64' of FIGS. 4A and 4B permits locking of stapler device 110 relative to pivot arm 60, independent of opening and closing of anvil 120.

A locking mechanism for an end effector 100" according to another example is described with reference to FIGS. 5A and 5B. End effector 100" is similar to end effectors 100 and 100', e.g., may include stapler device 110 and pivot arm 60. The locking mechanism may include a ball-nose spring plunger 64", including a housing 150 fixed to body 130 of stapler device 110. Ball-nose spring plunger 64" may include detents 64c" (notches) disposed on a distal end of pivot arm 60, a biasing member 64a" (e.g., a spring, a threaded housing having a spring and a ball-bearing or a plunger, or any other biasing member) disposed in (or on) housing 150 and configured to extend out of a proximal end of housing 150, and a ball bearing 64b". Ball bearing 64b" is inserted within an interior of biasing member 64a" so that ball bearing 64b" is held by biasing member 64a", rotates relative to biasing member 64a", and protrudes from an end of biasing member 64a".

As described herein, movement of elongated body 50 relative to pivot arm 60 may rotate end effector 100" about the axis defined by pin 60a. Distal movement of elongated body 50 may increase angle α and may cause biasing member 64a" to be compressed within housing 150. For example, as angle α increases, stapler device 110 rotates about the axis defined by pin 60a, which may cause the protruding material between detents 64c" (teeth) to push against ball bearing 64b", thereby compressing biasing member 64a" into housing 150. Biasing member 64a", ball bearing 64b", and detents 64c" may cooperate to lock stapler device 110 at different orientation angles α relative to pivot arm 60. For example, a friction force holds ball bearing 64b" within the corresponding detent 64c". As stapler device 110 is rotated about the axis defined by pin 60a, biasing member 64a" is compressed until the friction force between detent 64c" and ball bearing 64b" is overcoming. Overcoming this friction force causes ball bearing 64b" to move from the first detent 64c" to a second detent 64c", adjacent the first detent 64c". Once ball bearing 64b" moves to the second detent 64c", biasing member 64a" expands back to the original length/position. Additional distal movement of elongated body 50 may cause stapler device 110 to pivot about the pivot axis defined by pin 60a, causing biasing member 64a" to again compress. As biasing member 64a" is compressed, ball bearing 64b" is moved from the second detent 64c" to a third detent 64c", adjacent the second detent 64c". Continued distal movement of elongated body 50 causes angle α between axes A-A and B-B to increase. Alternatively, or additionally, the distal end of end effector 100" may be pushed against tissue to provide additional leverage and assist in changing angle α.

To decrease angle α, a force on elongated body 50 in the proximal direction (e.g., a pulling force) must be sufficient to overcome the frictional forces between ball bearing 64b" and detents 64c". When the friction force is overcome, stapler device 110 moves relative to pivot arm 60 such that angle α decreases. The number of detents 64c" and the spacing between adjacent detents 64c" may be selected based on the number of possible positions stapler device 110 may be locked relative to pivot arm 60. A smaller ball bearing and smaller detents may result in finger adjustments of angle α and more options for angle α.

A method of operating end effector 100" will now be described. End effector 100" may be introduced to the body and advanced to the target site in a similar manner as end effectors 100 and 100'. End effector 100 is advanced to the target site in a closed position and is opened by actuation of actuation wire 40a. During insertion, ball bearing 64b" may be engaged with a first detent 64c" so that angle α is approximately 0 degrees, e.g., so that axes A-A and B-B are approximately parallel. Once end effector 100" is adjacent the target site, the user may rotate stapler device 110 about the pivot axis defined by pin 60a by pushing elongate member 50 in the distal direction. The distal movement of elongate member 50 may cause angle α to increase and may cause biasing member 64a" to compress within housing 150. As biasing member 64a" is compressed from the original length into housing 150, a second detent 64c", adjacent to the first detent 64c", engages ball bearing 64b" and biasing member 64a" expands to the original length. Friction forces between ball bearing 64b" and the second detent 64c" lock stapler device 110 relative to pivot arm 60. The user may continue to push elongated member 50 in the distal direction until a desired orientation of stapler device 110 relative to pivot arm 60, e.g., a desired angle α, is achieved.

To decrease the angle α, elongated member 50 may be pulled in a proximal direction. Such movement causes spring 64b" to be compressed into housing 150, moving ball bearing 64b" from, e.g., the second detent 64c" to the first detent 64c". In this manner, the orientation of stapler device 110 relative to pivot arm 60 may be selected and locked. Locking mechanism 64" of FIGS. 5A and 5B permits locking and unlocking of stapler device 110 relative to pivot arm 60, independent of opening and closing of anvil 120.

It will be understood that any of the locking mechanisms described herein may be used alone or in combination with one or more other locking mechanisms described herein.

While different medical systems have been described, it will be understood that the particular arrangements of elements in these fastening systems are not limited. Moreover, a size, a shape, and/or the materials of the fastening system are not limited. As described herein, there are included various locking mechanisms for maintaining an orientation of a fastening device of an end effector. For example, in certain procedures, performing various medical procedures may be improved by ensuring proper orientation of the end effector relative to the endoscope and, thus, relative to the target site/tissue.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
an end effector at a distal end of the medical device;
an actuator coupled to a proximal end of the end effector;
a pivot arm pivotally coupled to the end effector distal of the proximal end of the end effector, wherein the pivot arm includes:
   a first opening at a proximal end of the pivot arm;
   a second opening in a sidewall of the pivot arm; and
   a lumen extending from the first opening to the second opening;
wherein the actuator is configured to extend through each of the first opening, the lumen, and the second opening, and wherein actuation of the actuator pivots the end effector relative to the pivot arm; and
a lock on the end effector and the pivot arm, wherein the lock has a first state permitting the end effector to pivot relative to the pivot arm and a second state restricting the end effector from pivoting relative to the pivot arm.

2. The medical device of claim 1, wherein the end effector includes a pair of jaws including a first jaw, and a second jaw hingedly connected to the first jaw and configured to move between an open position and a closed position.

3. The medical device of claim 2, wherein the lock is in the first state when the pair of jaws is in the open position, and the lock is in the second state when the pair of jaws is in the closed position.

4. The medical device of claim 2, wherein the end effector is configured to pivot independently of a movement of the first jaw relative to the second jaw.

5. The medical device of claim 1, wherein the lock includes:
a plurality of teeth at a distal end of the pivot arm, wherein the plurality of teeth define a plurality of spaces; and
a tab connected to the end effector, wherein the tab is configured to engage a space from the plurality of spaces in the second state.

6. The medical device of claim 1, wherein the lock includes:
a sprocket connected to the pivot arm, wherein the sprocket includes a plurality of teeth defining a plurality of spaces; and
a pawl pivotally connected at the proximal end of the end effector and configured to engage the plurality of spaces.

7. The medical device of claim 6, further comprising a wire connected to the pawl and extending in a proximal direction, wherein the pawl is biased into engagement with the plurality of spaces of the sprocket, and wherein moving the wire in the proximal direction is configured to pivot the pawl away from the sprocket to disengage the pawl from the plurality of spaces.

8. The medical device of claim 6, wherein the sprocket is arc shaped, and wherein a convex arrangement of the plurality of spaces of the sprocket faces proximally.

9. The medical device of claim 1, wherein the lock includes a ball-nose spring plunger.

10. The medical device of claim 9, wherein the ball-nose spring plunger includes:
a spring coupled at a first end of the end effector, wherein the spring is configured to extend from the first end and compress along a compression axis;
a plurality of detents fixed to the pivot arm; and
a ball bearing connected to the spring and selectively engaging each of the plurality of detents, wherein the ball bearing is configured to move along the compression axis.

11. The medical device of claim 10, wherein the ball bearing is configured to move from a first detent of the plurality of detents to an adjacent, second detent of the plurality of detents as the end effector pivots about the pivot arm, and wherein the spring is configured to be compressed from a first position to a second position and expand back to the first position as the ball bearing moves from the first detent to the second detent.

12. The medical device of claim 1, further comprising an actuation wire fixed to a proximal end of the end effector, wherein actuation of the actuation wire is configured to move the end effector between an open position and a closed position.

13. The medical device of claim 1, further comprising:
a handle assembly configured to actuate the end effector and the lock, wherein a proximal end of the actuator is connected to a distal end of the handle assembly; and
a catheter including at least one lumen and extending distally from the handle assembly,
wherein the actuator extends through the at least one lumen, and wherein the pivot arm is fixed to a distal end of the catheter.

14. The medical device of claim 1, wherein a pivot angle is defined between a longitudinal axis of the end effector and a longitudinal axis of the pivot arm, wherein a distal movement of the actuator is configured to increase the pivot angle, and wherein a proximal movement of the actuator is configured to decrease the pivot angle.

* * * * *